United States Patent
Konopa

(10) Patent No.: US 8,215,837 B2
(45) Date of Patent: Jul. 10, 2012

(54) INTEGRATED PATIENT POSITIONING AND RADIATION QUALITY ASSURANCE SYSTEM AND METHOD

(75) Inventor: Kenneth D. Konopa, Mercer Island, WA (US)

(73) Assignee: Fluke Corporation, Everett, WA (US)

( * ) Notice: Subject to any disclaimer, the term of this patent is extended or adjusted under 35 U.S.C. 154(b) by 196 days.

(21) Appl. No.: 12/203,714

(22) Filed: Sep. 3, 2008

(65) Prior Publication Data

US 2010/0054424 A1    Mar. 4, 2010

(51) Int. Cl.
*A61B 6/04* (2006.01)

(52) U.S. Cl. ........................................ 378/209; 378/207

(58) Field of Classification Search .................. 378/209, 378/167, 177, 189, 208, 7; 5/601, 943
See application file for complete search history.

(56) References Cited

U.S. PATENT DOCUMENTS

| | | | | |
|---|---|---|---|---|
| 3,891,850 A | * | 6/1975 | Bridgeman | 378/173 |
| 4,352,197 A | * | 9/1982 | Waerve | 378/177 |
| 5,226,068 A | * | 7/1993 | Strawder | 378/177 |
| 5,473,664 A | * | 12/1995 | Strawder | 378/177 |
| 5,943,390 A | * | 8/1999 | Wendlandt et al. | 378/189 |
| 6,163,902 A | * | 12/2000 | Mollette et al. | 5/601 |
| 7,144,158 B2 | * | 12/2006 | Dippl et al. | 378/177 |
| 2004/0001571 A1 | * | 1/2004 | Jahrling | 378/209 |
| 2004/0037390 A1 | * | 2/2004 | Mihara et al. | 378/65 |
| 2005/0058257 A1 | * | 3/2005 | Fischer et al. | 378/196 |
| 2006/0002519 A1 | * | 1/2006 | Jenkins et al. | 378/207 |
| 2006/0016006 A1 | * | 1/2006 | Whitmore et al. | 5/601 |

FOREIGN PATENT DOCUMENTS

JP      06189945 A   *   7/1994

* cited by examiner

*Primary Examiner* — Hoon Song
*Assistant Examiner* — Mona M Sanei
(74) *Attorney, Agent, or Firm* — Christensen O'Connor Johnson Kindness PLLC

(57) ABSTRACT

High intensity x-ray radiation therapy is used in the medical industry to treat tumors. Patients typically receive radiation treatment over a period of time, in which a quality assurance test of the x-ray beam is performed before each treatment. These quality assurance tests are performed by a detection device that receives the x-ray beam and measures the intensity, shape and uniformity of the x-ray beam. The integrated patient positioning and radiation quality assurance system includes recess assemblies into which an x-ray detection device is inserted to fix the location of the x-ray detection device on the board. As a result, the accuracy of the quality assurance test is improved and the set up time is reduced.

20 Claims, 5 Drawing Sheets

INTEGRATED PATIENT POSITIONING AND RADIATION QUALITY ASSURANCE SYSTEM AND METHOD

TECHNICAL FIELD

This invention relates to radiation therapy, and more particularly this invention relates to a quality assurance device used to calibrate a patient's radiation treatment dosage.

BACKGROUND OF THE INVENTION

Radiation therapy is often used in the medical industry as treatment for tumors. Radiation therapy is the process of using high energy x-rays or other energy sources to kill cancer cells and to shrink tumors.

In radiation treatment, the radiation beam may be wide with low intensity, resulting in large areas beyond the tumor being exposed to the radiation, or narrowly focused on the tumor with high intensity. For high intensity radiation treatment, the radiation beam is narrowly focused onto the tumor in order to minimize risks to healthy cells. The intensity of the radiation may vary depending on the type and size of the tumor. Therefore, in order to control the patient's dosage, it is necessary to control the beam's intensity, shape, and uniformity.

Generally, radiation therapy includes multiple treatments over a period of time. In order to maintain control over the dosage, quality assurance tests are performed before each treatment. Because each patient receives multiple treatments over a period of time and each treatment requires a quality assurance test to be performed on the radiation beam prior to exposing the tumor to the radiation, there is a need to maintain repeatability between treatments for each individual patient.

Radiation quality assurance tests are performed in the same environment that patients are treated, on patient positioning systems that includes a radiation-transparent board such as Halcyon™ patient positioning systems. Typically, quality assurance tests have been performed by positioning an x-ray detection device, such as the Thebes® and the Double Check Pro® x-ray detection devices sold by Fluke, Inc., into a bracket that is placed at any location onto the board. The table is then moved so that the x-ray detection device is aligned with the beam. At this location the shape, uniformity, and intensity of the beam is calibrated using the x-ray detection device.

Once the beam has been calibrated, the x-ray detection device is removed from the table. The patient is then placed on the table, and an attempt is made to position the patient so that the tumor is at the same location on the table at which the x-ray detection device was positioned. However, in order to align the x-ray beam to the tumor, it is necessary to determine the location of the calibration point. Unfortunately, insofar as the x-ray detection device is removed from the table when the patient is placed on the table, it can be difficult to position the patient so the tumor is at the proper location. Furthermore, because the x-ray detection device may be placed at different locations on the board for each calibration, the coordinates of the tumor relative to the calibration point must be calculated during each visit for the same patient. Therefore, it is difficult to ensure repeatability for recurring treatments of each individual patient. Also, the need to recalculate the coordinates of the tumor relative to the calibration point significantly slows the quality assurance process procedures. In addition, there may be less dosage consistency from treatment to treatment because the manual process of recalculating the coordinates of the tumor relative to the calibration point at each visit may result in errors.

Therefore, there is a need for a quality assurance system and process that is repeatable for each patient on recurring treatments in order to speed up the process and increase the accuracy of radiation treatments.

SUMMARY OF THE INVENTION

A quality assurance device used prior to radiation treatment to measure high energy x-rays is integrated with a patient positioning system. The patient positioning system includes at least one recess within a board on which a patient lies when receiving the radiation treatment. The recess is configured to accept an x-ray detection device that is used for quality assurance tests prior to each radiation treatment.

DETAILED DESCRIPTION

Embodiments of the present invention are directed toward providing repeatability to a quality assurance system and method for radiation treatment. Certain details are set forth below to provide a sufficient understanding of the invention. However, it will be clear to one skilled in the art that the invention may be practiced without these particular details.

Figure 1:
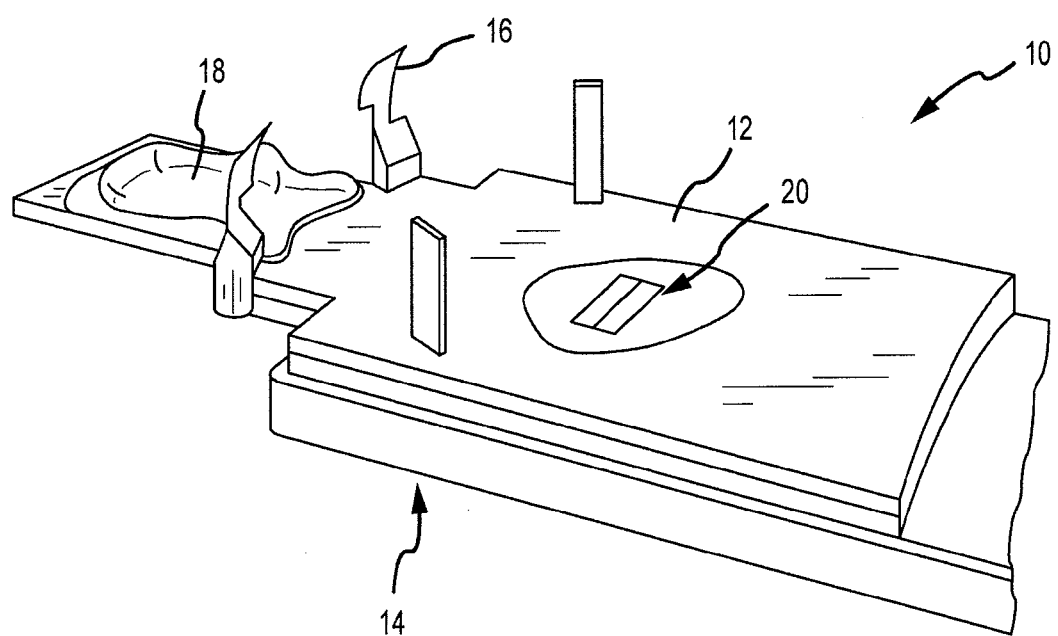
FIG. 1 is an isometric view of a patient-positioning board that includes a head board positioning system with a cutout showing the recess unit in the first surface of the board.

A quality assurance radiation treatment system and method according to one embodiment of the invention includes a patient positioning board 10 as shown in FIG. 1. The board 10 has an opposing first side and second side 12, 14, respectively, that are substantially parallel with one another. The first side 12 of the board 10 provides a surface for the patient to lie down upon when receiving radiation treatment. The board 10 is made from a radiation-transparent material and is generally metal free in order to minimize scattering of the x-rays. In one embodiment, the board 10 is made from carbon fiber, but it may be made from other translucent materials. In one embodiment, the thickness of the board 10 may be from 0.75 inches to 1.5 inches. In another embodiment, the board 10 is of a preferred thickness of 0.9 inches±0.06 inches.

When the patient lies on the first side 12 of the board 10, the patient may be held in position by a positioning system. In one embodiment, as shown in FIG. 1, the positioning system is a head board 18. In that embodiment a shoulder depression system 16 is used to stabilize the position of the upper body of the patient. In addition, in order to hold the patient's head in position, a perforated head mask (not shown) may be placed over the patient's face and attached to the head board 18. Other positioning systems may be used, such as breast board positioning system, a pelvis board positioning system, or some other patient positioning system.

Figure 2:
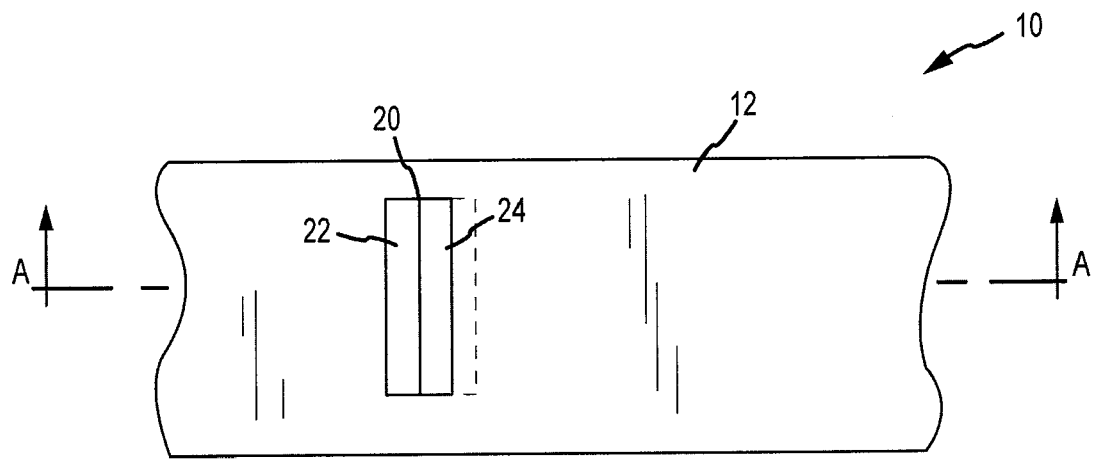
FIG. 2 is a top plan view of the patient positioning board of FIG. 1 showing one embodiment of a recess in the board for receiving a radiation calibration device.
Figure 3:
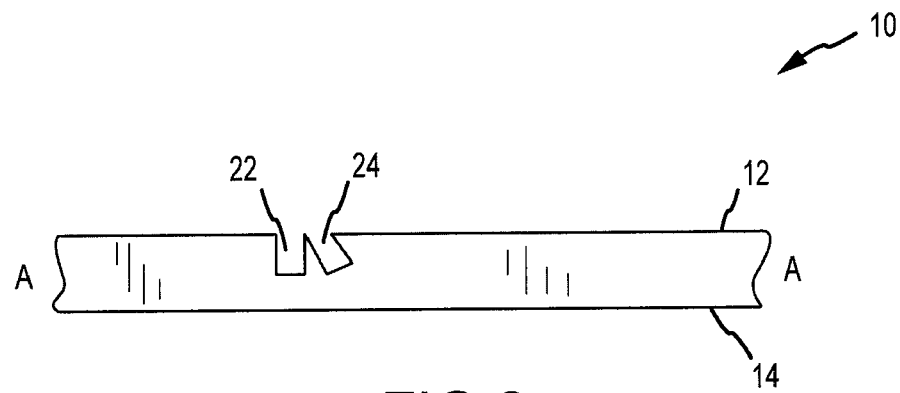
FIG. 3 is a cross sectional view of the patient positioning board, including the recess, taken along the line A-A of FIG. 2.

As shown in FIGS. 2 and 3, a recess assembly 20 is formed in the first side 12 of the board 10. Each recess assembly 20 includes a first recess 22 and a second recess 24 each of which is configured to accept an x-ray detection device (not shown in FIGS. 2 and 3). The location of the recess assembly 20 on the board 10 may be at any location on the first side 12 of the board 10. In one embodiment, the recess assembly 20 is located in the center of the first side 12 of the board 10. In another embodiment, a plurality of recess assemblies 20 are at different positions on the first side 12 of the board 10 so that a detection device could be placed into any one of the plurality of positions.

The first recess 22 holds the detection device in a position so that a detection device is perpendicular with the first side 12 of the board 10. The second recess 24 holds a detection device in a position so that the detection device is at an angle of 45° with the first side 12 of the board 10. The location of the first recess 22 relative to the second recess 24 may be of a variety of different configurations. In the embodiment shown in FIGS. 2 and 3, the first recess 22 is adjacent to the second recess 24. In another embodiment shown in FIGS. 4 and 5, the first recess 22 is positioned at a distance from the second recess 24. Although only two configurations are shown, many other configurations may be used.

Figure 4:
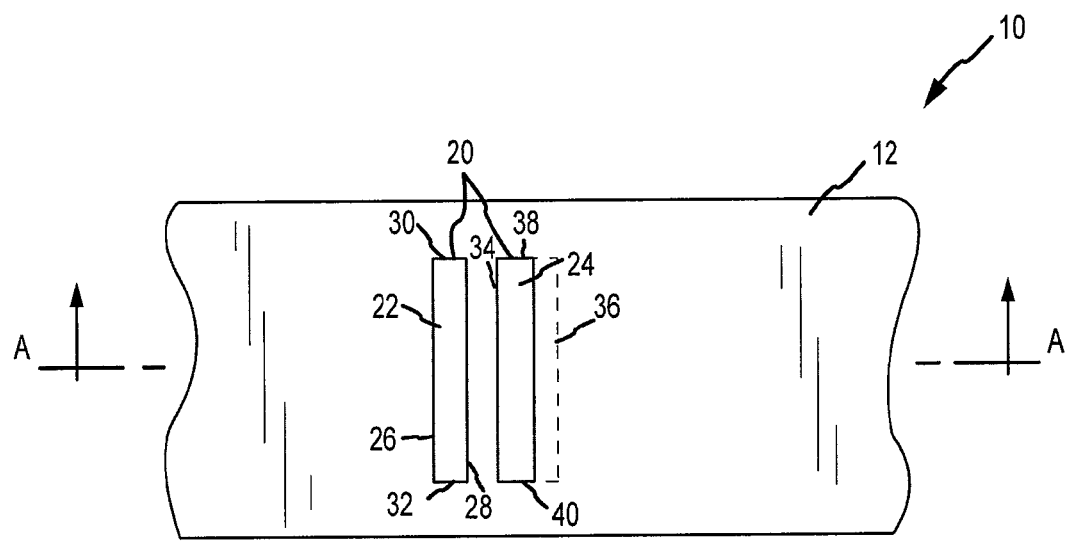
FIG. 4 is a top plan view of the first patient positioning board of FIG. 1 showing another embodiment of a recess in the board for receiving a radiation calibration device.
Figure 5:
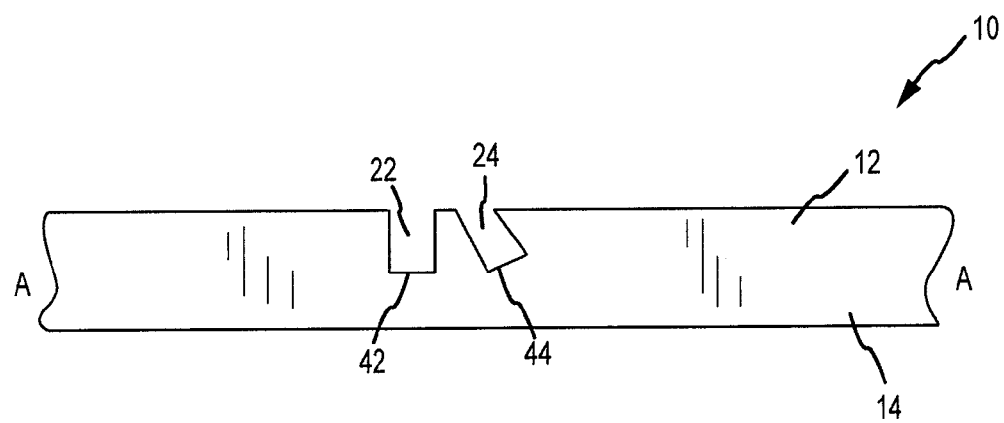
FIG. 5 is a cross sectional view of the patient positioning board, of FIG. 1, including the recess, taken along the line A-A of FIG. 4.

As shown in FIG. 4, the first recess 22 is defined by first and second opposing long sides 26, 28, respectively, and first and second opposing short sides 30, 32, respectively. The first long side 26 is substantially parallel with the second long side 28, and the first short side 30 is substantially parallel with the second short side 32. In addition, the first and second long sides 26, 28 are substantially at right angles with the first and second short sides 30, 32. In one embodiment, each recess 22, 24 extends into the board 10 to a depth less than the thickness of the board. The base of the recess 42 is shown in FIG. 5 as being flat; however, the base can be configured to other shapes, such as curved.

Similarly, the second recess 24 of the recess unit 20 is defined by a first and second opposing long side 34, 36, respectively, and a first and second opposing short side 38, 40, respectively. The first long side 34 is substantially parallel with the second long side 36, and the first short side 38 is substantially parallel with the second short side 40. In addition, the first and second long sides 34, 36 are substantially at right angles with the first and second short sides 38, 40. The first and second long side 34, 36 and the first and second short side 38, 40 extend into the board 10 at approximately a 45° angle measured from the first side 12 of the board 10 to a depth less than the thickness of the board. The base of the recess 44, as shown in FIG. 5, may be at an angle of 45° or less with the first side 12 of the board 10, parallel with the first side 12 of the board 10, concave in shape, or any other configuration.

Figure 6:
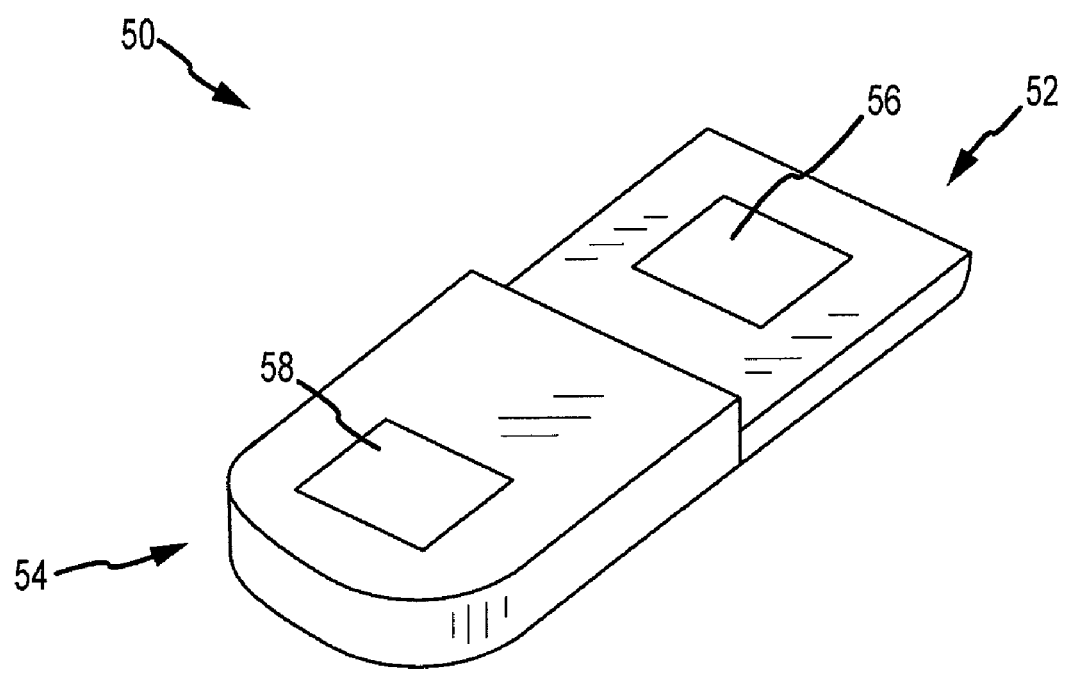
FIG. 6 is an isometric view showing one example of an x-ray detection device that may be used with a patient position board according to various embodiments of the invention.

The recess unit 20 is configured to accept a variety of different types of x-ray detection devices. The detection device may be fully integrated, including a sensor and a display panel, it may be wireless in which signals corresponding to measurements are transmitted to a remote device, or it may have some other configuration. Furthermore, the detection device may measure radiation in one or two dimensions. FIG. 6 shows a generic fully integrated detection device 50 that measures radiation in two dimensions. The detection device 50 includes a base 52, a top 54, a sensor 56 that intercepts the x-ray beam, and a display 58 that indicates the output. However, many other detection devices may be used. Example detection devices 50 include the previously-mentioned Thebes® device, which measures the beam linearly, the previously-mentioned Double Check Pro® Daily Check Device, and a INRTLog 2D Array, which is also available from Fluke, Inc., which measures the beam in a two dimensional array. However, many other types of radiation detection devices may be used.

Figure 7:
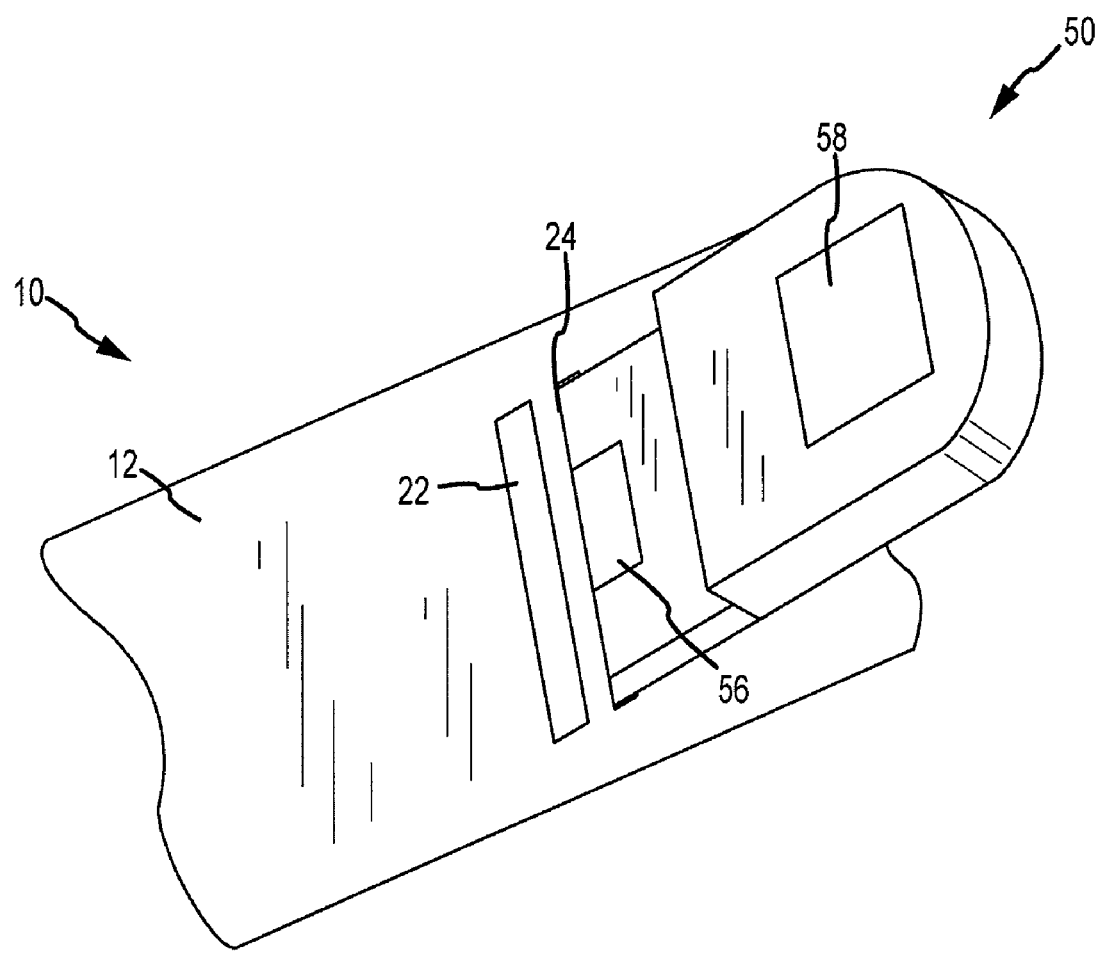
FIG. 7 is a side plan view showing the x-ray detection device of FIG. 6 located in a recess in the patient positioning board of FIGS. 4 and 5.

As shown in FIG. 7, the x-ray detection device 50 is placed into a recess 22 with the top 54 of the detection device 50 extending into the recess 22. The detection device 50 rests in the recess 22 so that the sensors 56 are generally aligned with the surface of the board 10. Once the x-ray detection device 50 is in position, it may be used to calibrate an x-ray beam. In one embodiment, the detection device 50 contains a sensor 56 made up of an ion chamber; however other detection devices 50 may use different types of sensors. Generally, the detection device 50 measures the x-ray beam's intensity, shape, uniformity, consistency, flatness, and/or total dosage; however, many other measurements may be obtained.

The detection devices 50 may measure the beam linearly or in two dimensions. A linear detection device 50 measures the beam intensity at multiple locations. When a linear detection device 50 is placed horizontally with the board 10, the detection device 50 measures the beam intensity linearly in the XY plane as shown in FIG. 2. When a linear detection device 50 is placed in first recess 22, the detection device 50 measures the beam intensity in the Z direction. Correspondingly, when a linear detection device 50 is placed in the second recess 24, the detection device 50 measures the beam intensity linearly in the XZ plane.

A two dimensional detection device 50 measures the beam intensity at multiple locations in a two dimensional array. When the two dimensional detection device 50 is placed horizontal with the board 10, the detection device 50 measures in the XY plane in both the X and Y direction. When the two dimensional detection device 50 is placed in the first recess 22, the detection device 50 measures the beam intensity in the XZ plane in both the X and Z direction. Correspondingly, when the two dimensional detection device 50 is placed in the second recess 24, the two dimensional detection device 50 measures in the XZ and YZ plane.

The detection device 50 uses each point measured on a particular plane, such as the XY plane, to calculate beam intensity, shape and uniformity. It is reasonably known in the art that uniformity remains fairly constant in parallel planes. Therefore, once multiple measurements have been made in a first plane, such as XY, only one measurement point is needed in a second parallel plane in the Z direction. From the measurements of a first XY plane and each individual measurement in a parallel plane in the Z direction, the uniformity in each parallel plane can be calculated. For example, if two measurements on the XY plane are XY1=1 and XY2=2, and a measurement on a second parallel plane in the Z direction is XYZ1=3, wherein XYZ1 is a point parallel to XY1, then XYZ2=6, wherein XYZ2 is a point parallel to XY2. Each point on the second parallel plane may be calculated to determine the uniformity on that plane. Based on the measurements taken, the beam is calibrated to the desired parameters.

Once the quality assurance test has been completed, the patient is placed onto the first side 12 of the board 10 in the appropriate positioning system. After the patient is secured into their position, the board 10 is moved to align the x-ray beam with the patient's tumor. Because the detection device is integrated into the board, the location of the beam during the quality assurance test is already predetermined. Typically, each patient receives repeated radiation treatments. Because the quality assurance tests are generally conducted at a fixed location and the tumor generally remains at a fixed location, the coordinates of the patient's tumor relative to the test location remains relatively constant. Therefore, for each patient receiving multiple treatments, the coordinates of the tumor relative to the quality assurance test location will generally only need to be calculated for the first treatment. Consequently, the test set up time is minimized for each subsequent treatment after the first treatment, and the repeatability between each treatment results in higher accuracy from treatment to treatment.

Although the present invention has been described with reference to the disclosed embodiments, persons skilled in the art will recognize that changes may be made in form and detail without departing from the spirit and scope of the invention. Such modifications are well within the skill of those ordinarily skilled in the art. Accordingly, the invention is not limited except as by the appended claims.

What is claimed is:

1. A device, comprising:
   a patient-positioning board having first and second ends and a substantially level surface between the first and second ends configured to accept a patient in a recumbent position;
   an x-ray detection device configured to receive and to measure an x-ray beam; and
   at least one recess between the first and second ends extending into the substantially level surface of the board, wherein the at least one recess forms a slot having opposing sidewalls that are spaced apart to receive a portion of the x-ray detection device, and when the x-ray detection device is placed into the recess, the x-ray detection device rests on a base that extends between the sidewalls of the slot, the at least one recess being configured to hold the x-ray detection device in a steady position at an acute angle relative to the substantially level surface in which the x-ray detection device protrudes from the substantially level surface.

2. The device of claim 1 wherein the board is manufactured from a carbon fiber.

3. The device of claim 1 wherein the at least one recess is a first recess, the device further comprising:
   a second recess, wherein the second recess is configured to accept the x-ray detection device at an angle perpendicular to the surface.

4. The device of claim 1 further comprising a plurality of recesses.

5. The device of claim 4 wherein the plurality of recesses are located on the surface of the board in pairs.

6. The device of claim 1 wherein the x-ray detection device is configured to linearly measure the x-ray beam.

7. The device of claim 1 wherein the x-ray detection device is configured to measure the x-ray beam within a plane.

8. The device of claim 1 wherein the board has a thickness greater than 0.75 inches.

9. The device of claim 1 wherein the surface comprises at least one of a shoulder depression system and a breast board positioning system.

10. The device of claim 1 wherein the board is fabricated from a radiation-transparent material.

11. The device of claim 1 wherein the at least one recess is configured to hold the x-ray detection device at an angle of approximately 45° relative to the substantially level surface of the board.

12. A device, comprising:
    a patient-positioning board having a surface with a substantially level portion between first and second edges; and
    at least one recess that extends into the level portion of the surface of the board,
    wherein the recess is configured with opposing sidewalls spaced apart to receive and hold an x-ray detection device in a steady position relative to the surface of the board such that a portion of the x-ray detection device extends out of the recess at an acute angle of relative to the level portion of the surface of the board.

13. The device of claim 12 wherein a plurality of recesses extend into the level portion of the surface of the board.

14. The device of claim 12 wherein the at least one recess is a first recess, the device further comprising a second recess, wherein the second recess is configured to accept an x-ray detection device at an angle perpendicular to the level portion of the surface.

15. The device of claim 12 wherein the recess is configured to receive and hold an x-ray detection device such that a portion of the x-ray detection device extends out of the recess at an angle of approximately 45° relative to the level portion of the surface.

16. A method of operating a quality assurance device, the method comprising:
    placing an x-ray detection device into a recess on a first surface of a patient-positioning board to extend the x-ray detection device out of the recess and to fix the position of the x-ray detection device at an angle of approximately 45° relative to the first surface of the patient-positioning board;
    aligning an x-ray beam with the detection device;
    measuring a characteristic of the x-ray beam using the x-ray detection device; and
    using the measured characteristic of the x-ray beam to calibrate the x-ray beam.

17. The method of claim 16 wherein the recess is a first recess, the method further comprising:
    placing the x-ray detection device into a second recess that is configured to fix the x-ray detection device approximately at an angle perpendicular to the first surface of the board.

18. The method of claim 16, further comprising:
    after measuring a characteristic of the x-ray beam using the x-ray detection device, removing the x-ray detection device from the board; and
    placing a patient on the board with a predetermined anatomical feature of the patient at a position on the board that is substantially the same as the position of the x-ray detection device relative to the board.

19. The method of claim 16 wherein measuring a characteristic of the x-ray beam comprises measuring an intensity of the x-ray beam.

20. The method of claim 16 wherein measuring a characteristic of the x-ray beam comprises measuring a shape of the x-ray beam.

* * * * *

UNITED STATES PATENT AND TRADEMARK OFFICE
CERTIFICATE OF CORRECTION

PATENT NO. : 8,215,837 B2  
APPLICATION NO. : 12/203714  
DATED : July 10, 2012  
INVENTOR(S) : K. D. Konopa Page 1 of 1

It is certified that error appears in the above-identified patent and that said Letters Patent is hereby corrected as shown below:

| COLUMN | LINE | |
|---|---|---|
| In the Claims | | |
| 6 | 17 | after "acute angle" delete "of" |
| Claim 12 | | |

Signed and Sealed this
Twenty-third Day of July, 2013

Teresa Stanek Rea
*Acting Director of the United States Patent and Trademark Office*